US00PP08168P

United States Patent [19]

Keen

[11] Patent Number: Plant 8,168

[45] Date of Patent: Mar. 2, 1993

[54] MIDFIELD BERMUDAGRASS

[75] Inventor: Ray A. Keen, Manhattan, Kans.

[73] Assignee: Kansas State University Research Foundation, Manhattan, Kans.

[21] Appl. No.: 706,272

[22] Filed: May 28, 1991

[51] Int. Cl.[5] ..... A01H 5/00

[52] U.S. Cl. ..... Plt./90

[58] Field of Search ..... Plt./88, 90

*Primary Examiner*—James R. Feyrer

*Attorney, Agent, or Firm*—Hovey, Williams, Timmons & Collins

[57] ABSTRACT

A triploid variety of Bermudagrass called Midfield, produces no viable seed, has superior cold hardness, excellent turf quality, and spreads more aggressively than most other turf type Bermudagrasses.

4 Drawing Sheets

BACKGROUND OF THE INVENTION

The present invention relates to a new and distinct variety of hybrid Bermudagrass which is well-adapted to the transition zone of the United States. Midfield is a turf-type hybrid Bermudagrass developed by open-pollination at the Kansas State University polycross nursery in Fort Hayes, Kans.

Bermudagrass is widely grown as a lawn and general purpose turf, as a forage plant, and for erosion control. Common Bermudagrass requires warm weather for growth. The devastating winter of 1989–1990 killed many acres of Bermudagrass, establishing a need for hardy selections possessing high turf quality, particularly in the northern Bermudagrass or transistion zone. In addition, current commercial Bermudagrass cultivars present certain problems in that they have poor sod strength and are not tolerant of low fertility.

The distinguishing characteristics of this new variety of plant are excellent cold hardiness combined with high turf quality at low nitrogen levels, that is to say, good texture, color, sod density and tensile strength. Midfield Bermudagrass possesses increased cold tolerance to −20° F. and is also very drought resistant. This cultivar is aggressive, tolerant of low fertility, and has excellent wear resistance, which makes it suitable for school grounds or other low maintenance use.

Midfield Bermudagrass is a clone which was vegetatively propagated from rhizomes or stolons. The cultivar originated from a single seedling and was vegetatively propagated at Manhattan, Kans. The seed parent of Midfield was a cold hardy, Kansas, common tetraploid ($2n=4\times=36$) Bermudagrass, *Cynodon dactlon* var. *dactylon*. The pollen parent was one of several African diploid ($2n=2\times=18$) Bermudagrasses, *C. transvaalensis*, growing in the same polycross nursery as the common parent. Midfield is a triploid with $2n=3\times=27$ chromosomes and is highly male and female sterile. The clone progeny have been shown to be stable in all distinguishing characteristics.

BRIEF DESCRIPTION OF THE DRAWING FIGURES

BOTANICAL DESCRIPTION OF THE PLANT

Figure 1:
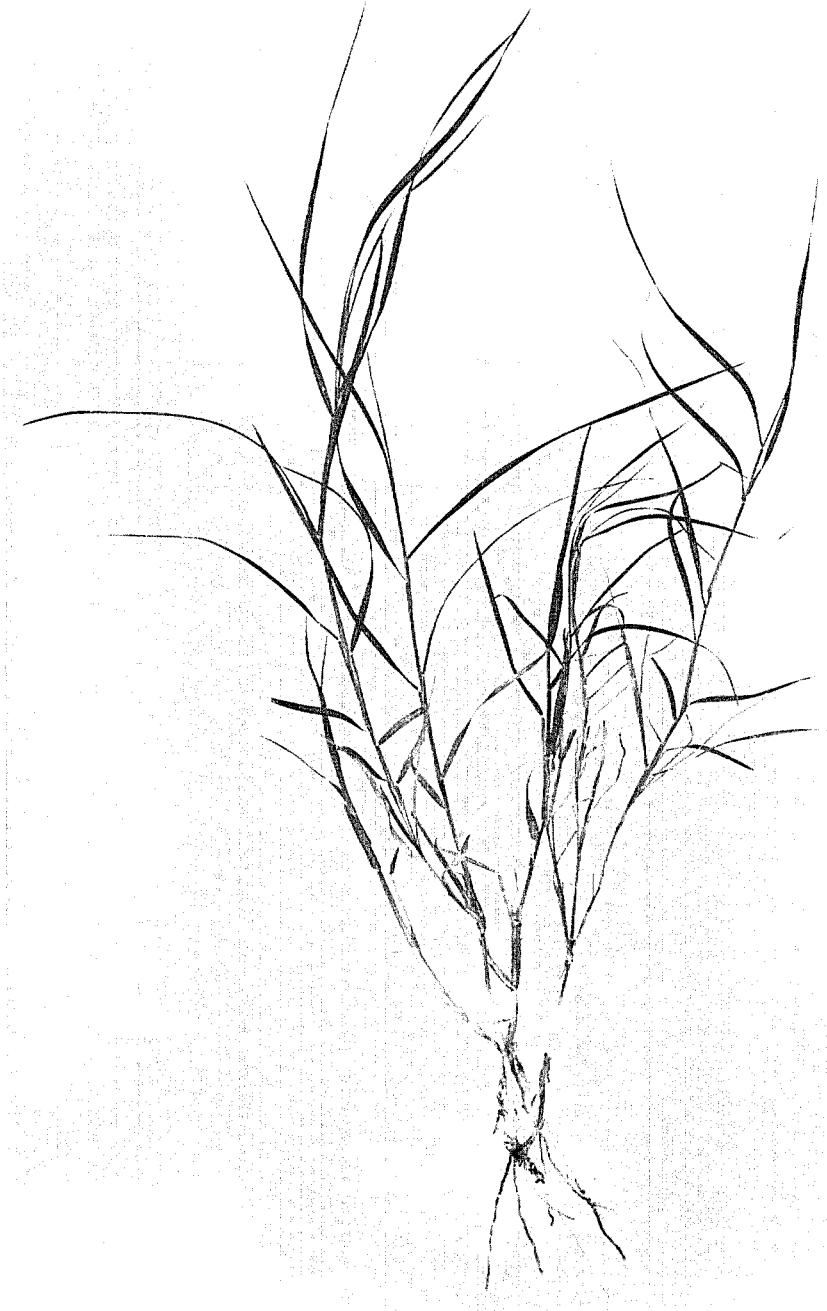
FIG. 1 is a color photographic representation of a nursery grown potted Midfield Bermudagrass plant in accordance with the invention.
Figure 2:
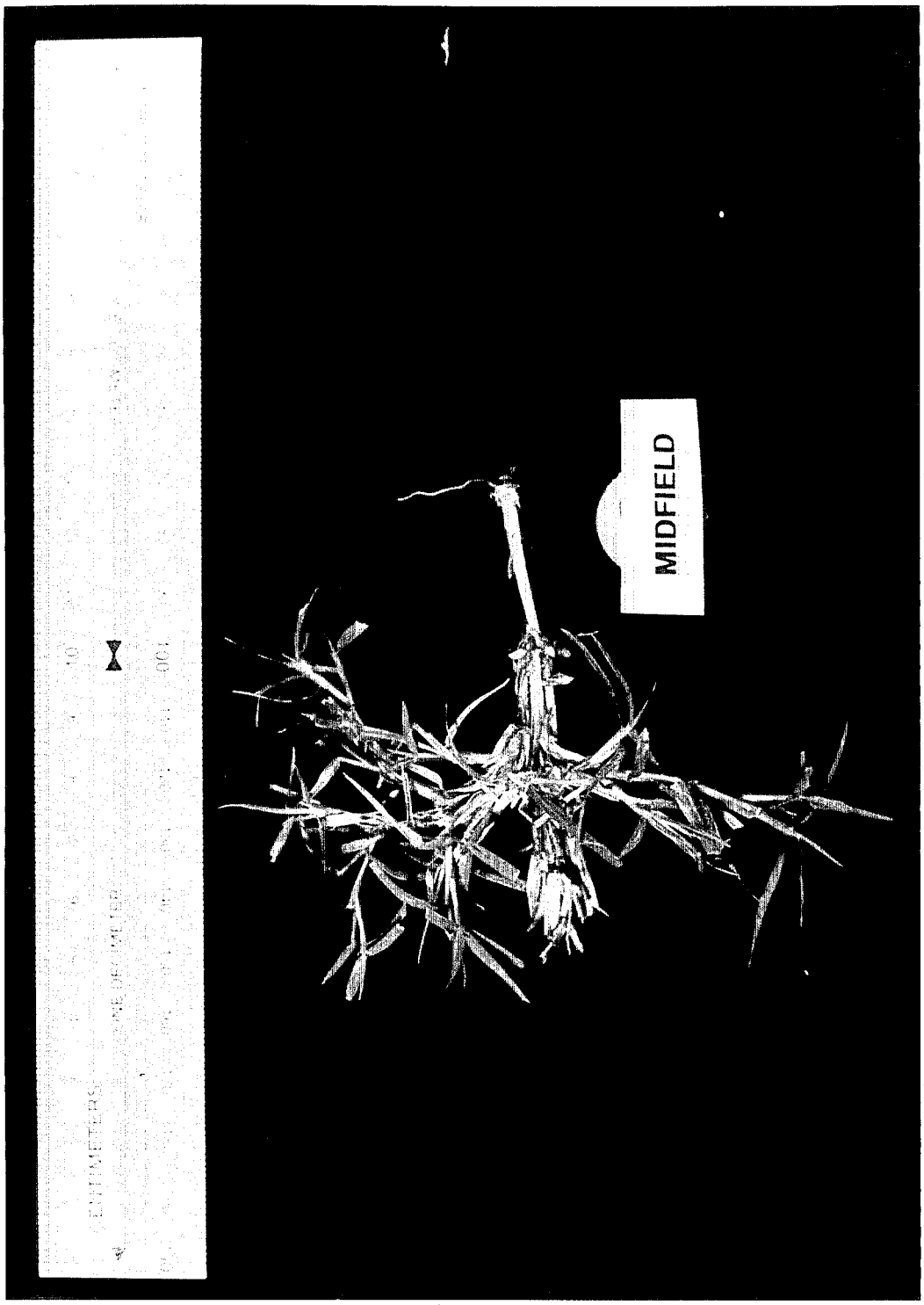
FIG. 2 is a color photographic representation of a field grown Midfield Bermudagrass plant subject to periodic mowing.

The following taxonomic description is of the plant when grown in the green house as a potted plant and describes specimens cultured under controlled conditions which can be reproduced. However, the description to follow should not be construed as limiting with regard to the expressed characteristics of this plant, because the characteristics of Midfield have been observed to vary widely as a function of stage of growth, growing conditions, geographic location of culture, and management practices to which sod of the plant is subjected. Such differences in appearance of this plant can be appreciated with a comparison of FIG. 1 and FIG. 2 of the drawing, for example.

MIDFIELD BERMUDAGRASS

'Midfield' Bermudagrass, *Cynodon dactylon*×*Cynodon transvaalensis* is a stoloniferous perennial with slender underground tan to light brown rhizomes; surface stolons slender, prostrate, fast spreading; culms slender, about 5–40 cm high and 0.5–1.5 mm in diameter. Leafblades flat, or folded when dry, often short and narrow, about 1.5–2.0 mm wide and 75–110 mm long on fuly extended mature shoots; leaves dark green, mostly glabrous with very few hairs on upper (adaxial) surface near base; ligule a membranous rim about 0.2–0.3 mm long, ciliate on the edge; leaf sheaths light green, sometimes deveoping purple (anthocyanin) pigmentation at base, glabrous except for few hairs at base, about 10–40 mm in length and 1–5 mm in width. Internodes light green, sometimes developing purple (anthocyanin) pigmentation. Midfield exhibits a dark park green leaf color, #21-L-8, Maerz et al., *A Dictionary of Color*, McGraw-Hill Book Company, 2 Ed. (1950). Inflorescences infrequent, seldom producing seed heads; no viable seed produced. Growth habit decumbent, prostrate.

Midfield is effectively sterile but does exhibit complete flower parts. Anthers are formed in the flowers;

however, little if any viable pollen is formed within the anthers.

Unmowed midfield exhibits an average internode length of from about 43.2 to 47 mm, and roots readily form at each node under favorable conditions of soil moisture and temperature.

Midfield has been experimentally tested at several locations in the United States for overall turf performance. It is superior to commercial turf Bermudagrass varieties in one or more of the following characteristics affecting turf performance: sod density, color, and cold-tolerance. Midfield, along with two other cultivars, showed the second highest frost tolerance rating of 28 cultivars tested. As compared with other seedless types, Midfield is an aggressive clone with good turf quality and sod strength at low nitrogen levels. Midfield is an aggressive, fast-growing cultivar exhibiting a growth rate comparable to Vamont and Midiron cultivars. Midfield produces fewer seed heads, especially at higher nitrogen levels. It is anticipated that Midfield will be used exclusively as a lawn grass and for recreational turfs; it is not anticipated that Midfield will be used as a forage grass. Midfield exhibits substantially similar mowing and thatching characteristics, as compared with conventional Bermudagrass cultivars.

Figure 3:
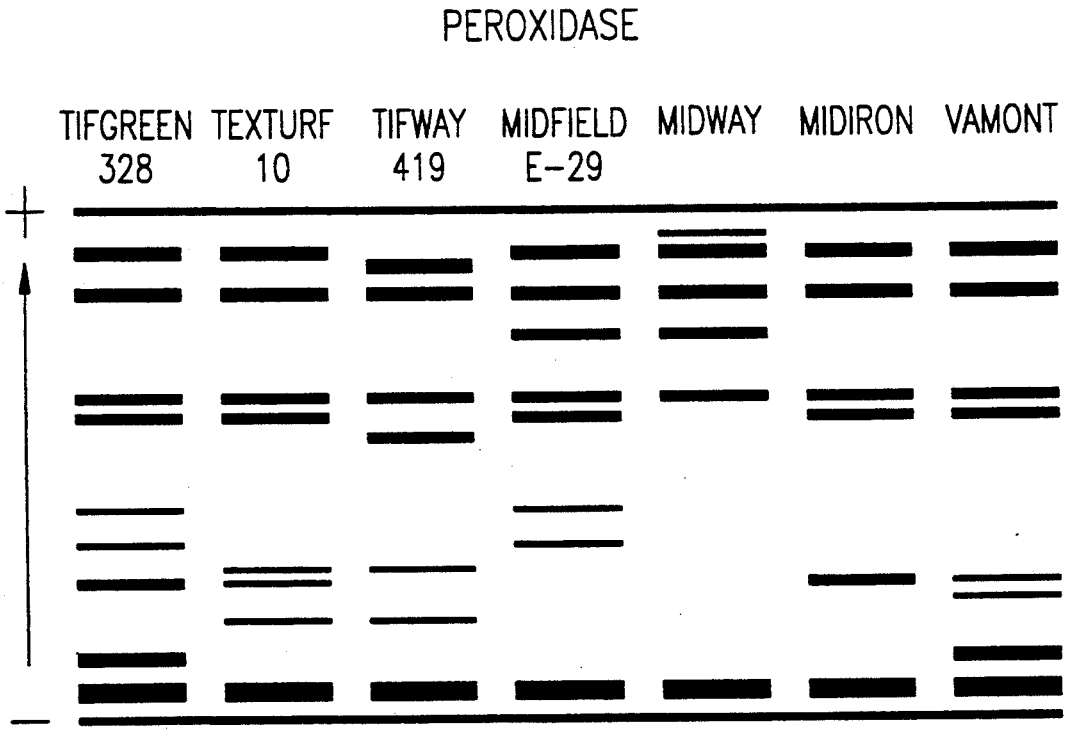
FIG. 3 is a graphic representation of electrophoretic banding patterns in the peroxidase isoenzyme system.
Figure 4:
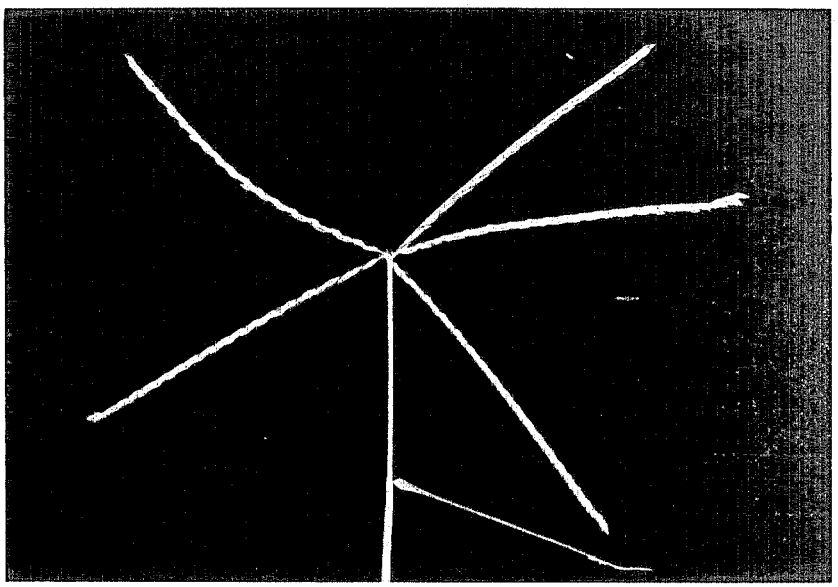
FIG. 4 is a photograph illustrating the complete influorescence of Midfield Bermudagrass.
Figure 5:
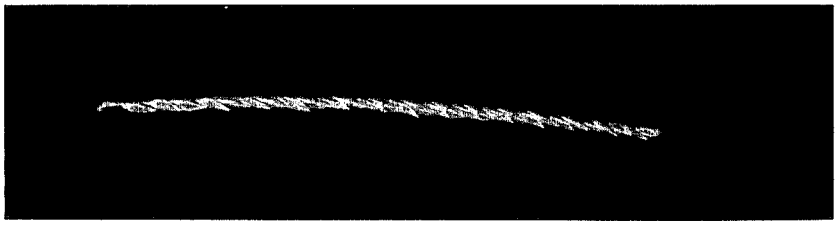
FIG. 5 is a photograph illustrating a single raceme of Midfield Bermudagrass.
Figure 6:
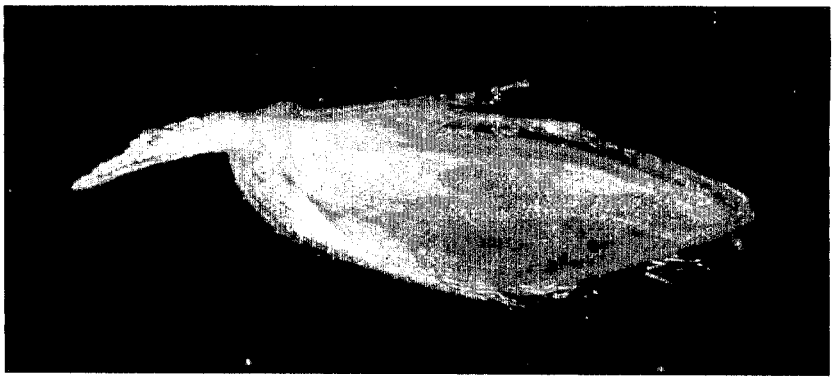
FIG. 6 is a photograph illustrating a single spikelet of Midfield Bermudagrass.

Midfield Bermudagrass is genetically and physiologically distinctive as compared to other turf Bermudagrass cultivars. As best shown in FIG. 3, Midfield presents distinct electrophoretic banding patterns in the peroxidase isoenzyme system. Moreover, Midfield exhibits inflorescence of unilateral racemes numbering 3–6, usually 4 or 5, 3.5–6 cm long (average 4.3 cm); spikelets perfect 2–2.5 mm long with medium spacing on raceme, about 2.5 mm; glumes lanceolate in side view, 1-nerved, the upper ½–⅔ as long as the spikelet; lemma pubescent on the keel; palea glabrous.

The outstanding characteristics of this new variety of Bermudagrass are greater cold-tolerance combined with good turf quality at low nitrogen levels. Midfield is an aggressive clone with good sod strength and wear resistance which is suitable for school grounds and other low maintenance use.

The following Tables 1–9 further describe the characteristics of Midfield (E-29), as compared with other cultivars. Tables 3 and 4 confirm the spring green-up and frost hardiness of Midfield. Table 9 demonstrates that Midfield is resistant to Spring Dead Spot (*Ophiosphaerella herpotrica*).

TABLE 1

Sod Quality of Bermudagrass Clones, 1987–88[1]

| Bermuda clone | Internode length (in.) | Rhizome depth | Sod strength (lbs.) 1978 | 1981 | (Kgs) 1988 |
|---|---|---|---|---|---|
| Midiron | 2.0 | 1.75 | 12.5 | 17.7 | 16.7 |
| KS Improved | 1.5 | 4.28 | 28.0 | 23.2 | NA |
| Midfield | 1.8 | 2.72 | 33.5 | 44.9 | 45.7 |
| Midlawn | 1.7 | 2.34 | 34.3 | 31.8 | 30.7 |

[1]Data for 1978 and 1981 from Kansas State University Research Center; 1988 data from Mississippi State University

TABLE 2

Mean Turfgrass Quality Ratings of Bermudagrass Cultivars at Thirteen Locations in the United States, 1990[1]

| Bermuda clone | Turfgrass Quality Ratings (1–9, 9 = ideal turf) AR | AZ | CA2 | CA3 | FL | KS | LA |
|---|---|---|---|---|---|---|---|
| Tifway | 7.9 | 7.9 | 6.7 | 6.4 | 7.9 | 1.0 | 7.6 |
| Tifway II | 7.8 | 7.8 | 6.4 | 6.4 | 8.1 | 1.5 | 7.7 |
| MSB-10 | 7.6 | 7.8 | 6.9 | 6.3 | 8.1 | 1.7 | 7.7 |
| A-29 | 7.1 | 6.9 | 5.5 | 5.5 | 6.4 | 8.2 | 7.1 |
| Midfield (E-29) | 7.0 | 6.4 | 5.6 | 5.7 | 6.6 | 8.0 | 6.2 |
| Midiron | 6.8 | 6.4 | 5.9 | 5.8 | 6.9 | 7.5 | 6.8 |
| Midlawn (A-22) | 7.1 | 6.6 | 5.5 | 5.9 | 5.9 | 7.7 | 6.6 |
| MSB-20 | 7.4 | 7.1 | 5.7 | 5.5 | 7.7 | 1.0 | 7.1 |
| NM 43 | 6.9 | 7.1 | 5.6 | 5.8 | 7.7 | 1.2 | 7.2 |
| MSB-30 | 6.0 | 6.9 | 6.5 | 5.8 | 6.5 | 2.7 | 7.1 |
| Tufcote | 7.6 | 6.2 | 5.7 | 5.7 | 7.2 | 2.0 | 7.4 |
| Tifgreen | 6.7 | 6.9 | 5.7 | 5.6 | 8.1 | 1.3 | 6.8 |
| CT-23 | 5.0 | 7.2 | 5.6 | 5.9 | 6.5 | 3.0 | 7.2 |
| NM 507 | 6.3 | 7.7 | 6.2 | 5.6 | 8.1 | 1.0 | 7.4 |
| Texturf 10 | 6.3 | 6.6 | 5.5 | 5.5 | 7.0 | 2.8 | 6.3 |
| NM 471 | 5.8 | 6.9 | 6.1 | 6.0 | 7.6 | 1.0 | 7.3 |
| RS-1 | 6.0 | 5.6 | 5.5 | 5.7 | 5.7 | 5.8 | 5.9 |
| FB-119 | 5.4 | 6.1 | 5.4 | 5.2 | 6.7 | 1.0 | 7.3 |
| NM 375 | 5.7 | 6.2 | 5.4 | 5.6 | 7.1 | 1.0 | 6.6 |
| Vamont | 5.5 | 5.4 | 5.2 | 5.3 | 6.7 | 3.2 | 5.7 |
| NMS 3 | 4.7 | 6.4 | 5.3 | 5.5 | 6.7 | 1.0 | 6.8 |
| NM 72 | 4.8 | 6.4 | 5.2 | 5.1 | 7.8 | 1.0 | 6.6 |
| NMS 4 | 5.6 | 6.3 | 5.5 | 5.3 | 7.2 | 1.0 | 6.2 |
| Guymon | 5.1 | 6.2 | 4.6 | 5.2 | 6.2 | 6.2 | 5.6 |
| Numex-Sahara | 4.7 | 4.7 | 5.2 | 5.1 | 4.9 | 1.0 | 6.3 |
| NMS 2 | 4.9 | 4.5 | 5.1 | 5.1 | 3.8 | 1.0 | 5.4 |
| NMS 14 | 4.5 | 4.6 | 4.9 | 4.8 | 4.6 | 1.0 | 5.2 |
| AZ Common | 4.6 | 4.2 | 4.8 | 4.9 | 4.4 | 1.0 | 5.4 |
| LSD VALUE | 1.1 | 0.6 | 0.4 | 0.4 | 1.1 | 1.4 | 0.6 |

TABLE 2-continued

Mean Turfgrass Quality Ratings of Bermudagrass Cultivars at Thirteen Locations in the United States, 1990[1]

| Bermuda clone | Turfgrass Quality Ratings (1–9, 9 = ideal turf) MD | MO | MS | UB | VA1 | VA4 | Mean |
|---|---|---|---|---|---|---|---|
| Tifway | 7.1 | 1.9 | 7.5 | 7.3 | 6.2 | 7.1 | 6.3 |
| Tifway II | 6.8 | 1.0 | 7.7 | 7.3 | 6.3 | 7.1 | 6.3 |
| MSB-10 | 6.8 | 1.0 | 7.7 | 6.7 | 6.3 | 6.8 | 6.3 |
| A-29 | 5.8 | 1.4 | 5.1 | 7.0 | 7.0 | 5.5 | 6.0 |
| Midfield (E-29) | 5.8 | 2.8 | 4.4 | 6.8 | 6.5 | 5.9 | 6.0 |
| Midiron | 5.3 | 2.7 | 4.2 | 6.3 | 6.2 | 5.8 | 5.9 |
| Midlawn (A-22) | 5.7 | 1.4 | 5.1 | 6.7 | 6.2 | 5.8 | 5.8 |
| MSB-20 | 6.3 | 1.0 | 6.9 | 7.6 | 5.5 | 6.6 | 5.8 |
| NM 43 | 6.2 | 1.0 | 6.7 | 7.7 | 6.2 | 6.1 | 5.8 |
| MSB-30 | 6.7 | 1.5 | 5.9 | 6.2 | 5.7 | 7.1 | 5.7 |
| Tufcote | 5.4 | 1.0 | 5.6 | 7.4 | 6.5 | 6.7 | 5.7 |
| Tifgreen | 5.9 | 1.0 | 6.2 | 7.8 | 6.0 | 6.4 | 5.7 |
| CT-23 | 6.4 | 1.0 | 5.6 | 5.7 | 4.8 | 6.2 | 5.4 |
| NM 507 | 6.2 | 1.0 | 4.5 | 4.3 | 4.8 | 6.9 | 5.4 |
| Texturf 10 | 5.5 | 1.0 | 4.7 | 5.8 | 6.3 | 6.3 | 5.4 |
| NM 471 | 5.8 | 1.0 | 4.4 | 4.8 | 5.2 | 6.9 | 5.3 |
| RS-1 | 5.3 | 1.5 | 3.7 | 5.8 | 5.7 | 5.6 | 5.2 |
| FB-119 | 5.8 | 1.2 | 4.6 | 6.3 | 6.3 | 6.0 | 5.2 |
| NM 375 | 5.2 | 1.0 | 4.0 | 6.1 | 5.8 | 6.0 | 5.1 |
| Vamont | 4.8 | 2.1 | 4.0 | 5.9 | 5.7 | 5.8 | 5.0 |
| NMS 3 | 5.7 | 1.0 | 3.8 | 5.9 | 5.5 | 6.2 | 5.0 |
| NM 72 | 5.4 | 1.0 | 4.5 | 5.4 | 4.8 | 6.2 | 4.9 |
| NMS 4 | 5.1 | 1.2 | 2.7 | 5.8 | 5.0 | 5.9 | 4.8 |
| Guymon | 4.8 | 2.6 | 2.2 | 5.1 | 3.2 | 3.0 | 4.6 |
| Numex-Sahara | 5.2 | 1.0 | 2.6 | 5.2 | 4.0 | 5.6 | 4.3 |
| NMS 2 | 5.3 | 1.0 | 2.4 | 5.4 | 3.8 | 5.4 | 4.1 |
| NMS 14 | 4.6 | 1.0 | 2.3 | 4.9 | 4.2 | 5.1 | 4.0 |
| AZ Common | 3.4 | 1.0 | 2.2 | 5.0 | 4.0 | 4.7 | 3.8 |
| LSD VALUE | 1.1 | 1.1 | 0.7 | 0.8 | 1.6 | 0.7 | 0.3 |

[1]In certain states tests were performed at more than one location, hence CA2 and CA3 for California and VA1 and VA4 for Virginia.

To determine statistical differences among entries, subtract one entry's mean from another. Statistical differences occur when this value is larger than the corresponding LSD value (LSD 0.05).

TABLE 3

Spring Greenup Rating of Bermudagrass Cultivars, 1990[1]

| Bermuda clone | Greenup Ratings (1–9, 9 = completely green) AR | AZ | FL | MS | Mean |
|---|---|---|---|---|---|
| MSB-20 | 5.7 | 6.0 | 5.3 | 5.7 | 5.7 |
| Midfield (E-29) | 6.0 | 6.3 | 5.0 | 4.0 | 5.3 |
| NM 43 | 5.3 | 6.3 | 4.3 | 5.0 | 5.3 |
| Midlawn (A-22) | 5.7 | 7.0 | 3.3 | 4.7 | 5.2 |
| Tifway | 5.0 | 6.3 | 4.3 | 5.0 | 5.2 |
| Vamont | 5.0 | 6.0 | 4.7 | 4.7 | 5.1 |
| MSB-10 | 3.7 | 6.0 | 5.0 | 5.0 | 4.9 |

TABLE 3-continued

Spring Greenup Rating of Bermudagrass Cultivars, 1990[1]

| Bermuda clone | Greenup Ratings (1–9, 9 = completely green) AR | AZ | FL | MS | Mean |
|---|---|---|---|---|---|
| Midiron | 5.3 | 6.3 | 2.7 | 5.0 | 4.8 |
| Tufote | 5.7 | 4.7 | 3.0 | 5.7 | 4.8 |
| Tifgreen | 5.0 | 5.3 | 4.3 | 4.3 | 4.8 |
| Tifway II | 4.0 | 5.0 | 4.7 | 5.0 | 4.7 |
| Texturf 10 | 3.7 | 6.3 | 4.0 | 4.0 | 4.5 |
| A-29 | 4.7 | 5.0 | 3.3 | 4.7 | 4.4 |
| RS-1 | 5.7 | 5.0 | 2.7 | 4.0 | 4.3 |
| FB-119 | 1.7 | 6.7 | 5.7 | 3.0 | 4.3 |
| NM 507 | 2.0 | 6.7 | 4.3 | 3.7 | 4.2 |
| Guymon | 5.7 | 5.0 | 3.3 | 2.0 | 4.0 |
| NM 375 | 2.7 | 5.7 | 4.0 | 3.3 | 3.9 |
| NM 72 | 2.0 | 5.3 | 4.3 | 4.0 | 3.9 |
| MSB-30 | 1.7 | 7.3 | 2.3 | 4.0 | 3.8 |
| NM 471 | 2.0 | 6.0 | 3.7 | 3.3 | 3.8 |
| AZ Common | 2.7 | 5.0 | 5.0 | 2.0 | 3.7 |
| NMS 4 | 2.3 | 5.3 | 2.7 | 2.3 | 3.2 |
| Numex-Sahara | 3.0 | 4.3 | 3.0 | 2.0 | 3.1 |
| NMS 14 | 2.7 | 4.7 | 2.3 | 2.0 | 2.9 |
| CT-23 | 1.0 | 4.7 | 1.3 | 3.0 | 2.5 |
| NMS 2 | 3.0 | 3.7 | 1.3 | 2.0 | 2.5 |
| NMS 3 | 1.3 | 3.7 | 2.0 | 2.3 | 2.3 |
| LSD VALUE | 1.3 | 1.4 | 1.5 | 1.0 | 0.6 |

[1]To determine statistical differences among entries, subtract one entry's mean from another. Statistical differences occur when this value is larger than the corresponding LSD value (LSD 0.05).

TABLE 4

Frost Tolerance Ratings of Bermudagrass Cultivars, 1990[1]

| Bermuda clone | Frost Tolerance Ratings (1–9, 9 = no injury) AR | VA | Mean |
|---|---|---|---|
| Tifway II | 9.0 | 7.3 | 8.2 |
| Tufcote | 8.7 | 6.7 | 7.7 |
| Tifway | 8.7 | 6.3 | 7.5 |
| CT-23 | 7.7 | 7.0 | 7.3 |
| MSB-10 | 9.0 | 5.0 | 7.0 |
| Midlawn (A-22) | 8.0 | 5.3 | 6.7 |
| Midfield (E-29) | 7.3 | 5.7 | 6.5 |
| MSB-30 | 8.7 | 4.0 | 6.3 |
| NM 375 | 4.7 | 7.7 | 6.2 |
| NM 507 | 7.0 | 4.7 | 5.8 |
| A-29 | 8.0 | 3.0 | 5.5 |
| NM 471 | 7.3 | 3.7 | 5.5 |
| FB-119 | 5.3 | 5.0 | 5.2 |
| NMS 2 | 5.3 | 4.7 | 5.0 |
| NMS 4 | 6.3 | 3.7 | 5.0 |
| Texturf 10 | 6.7 | 3.3 | 5.0 |
| AZ Common | 6.7 | 3.0 | 4.8 |
| NMS 3 | 5.7 | 4.0 | 4.8 |
| Numex-Sahara | 5.3 | 4.3 | 4.8 |
| NMS 14 | 5.0 | 3.7 | 4.3 |
| RS-1 | 5.0 | 3.3 | 4.2 |
| Midiron | 5.0 | 3.0 | 4.0 |
| NM 72 | 4.3 | 3.7 | 4.0 |
| Tifgreen | 5.7 | 2.3 | 4.0 |
| Vamont | 2.7 | 5.3 | 4.0 |
| Guymon | 4.7 | 3.0 | 3.8 |
| NM 43 | 5.0 | 2.3 | 3.7 |
| MSB-20 | 5.0 | 2.0 | 3.5 |
| LSD VALUE | 1.5 | 1.3 | 1.0 |

[1]To determine statistical differences among entries, subtract one entry's mean from, another. Statistical differences occur when this value is larger than the corresponding LSD value (LSD 0.05).

TABLE 5

Winter Kill Rating of Bermudagrass Cultivars, 1990[1]

| Bermuda clone | Percent Winter Kill: Locations IL | MO | UB | Mean |
|---|---|---|---|---|
| NM 507 | 99.0 | 99.0 | 84.7 | 94.2 |
| NM 471 | 99.0 | 99.0 | 81.7 | 93.2 |
| C1-23 | 99.0 | 99.0 | 80.0 | 92.7 |
| NMS 14 | 99.0 | 99.0 | 73.3 | 90.4 |
| AZ-Common | 99.0 | 99.0 | 70.0 | 89.3 |
| NM 72 | 99.0 | 99.0 | 61.7 | 86.6 |

TABLE 5-continued

Winter Kill Rating of Bermudagrass Cultivars, 1990[1]

| Bermuda clone | Percent Winter Kill: Locations IL | MO | UB | Mean |
|---|---|---|---|---|
| NMS 4 | 99.0 | 98.7 | 56.7 | 84.8 |
| Numex-Sahara | 99.0 | 99.0 | 51.7 | 83.2 |
| NMS 2 | 99.0 | 99.0 | 50.0 | 82.7 |
| FB-119 | 99.0 | 98.7 | 48.3 | 82.0 |
| NMS 3 | 99.0 | 99.0 | 45.0 | 81.0 |
| MSB-30 | 99.0 | 94.3 | 46.7 | 80.0 |
| Texturf 10 | 99.0 | 98.7 | 28.3 | 75.3 |
| NM 375 | 99.0 | 99.0 | 26.7 | 74.9 |
| Tifway II | 99.0 | 99.0 | 23.3 | 73.8 |
| MSB-10 | 99.0 | 99.0 | 21.7 | 73.2 |
| Tifway | 99.0 | 94.0 | 18.3 | 70.4 |
| NM 43 | 99.0 | 99.0 | 10.0 | 69.3 |
| MAV-20 | 99.0 | 99.0 | 8.3 | 68.8 |
| Tifgreen | 99.0 | 99.0 | 8.3 | 68.8 |
| Midlawn (A-22) | 99.0 | 97.7 | 0.0 | 65.6 |
| RS-1 | 99.0 | 96.0 | 1.7 | 65.6 |
| A-29 | 99.0 | 96.0 | 0.0 | 65.0 |
| Tufcote | 89.3 | 99.0 | 0.0 | 62.8 |
| Guymon | 97.7 | 76.7 | 13.3 | 62.6 |
| Vamont | 86.0 | 81.3 | 0.0 | 55.3 |
| Midiron | 99.0 | 67.0 | 0.0 | 55.3 |
| Midfield (E-29) | 99.0 | 59.7 | 0.0 | 52.9 |
| LSD VALUE | 8.6 | 24.6 | 23.9 | 11.8 |

[1]To determine statistical differences among entries, subtract one entry's mean from another. Statistical differences occur when this value is larger than the corresponding LSD value (LSD 0.05).

TABLE 6

Genetic Color Ratings of Bermudagrass Cultivars, 1990[1]

| Bermuda clone | Genetic Color Ratings (1–9, 9 = dark green) AR | AZ | CA2 | CA3 | LA | TX | Mean |
|---|---|---|---|---|---|---|---|
| Tifway II | 7.3 | 7.3 | 8.0 | 8.0 | 8.7 | 9.0 | 8.1 |
| Tifway | 7.7 | 7.3 | 8.0 | 7.7 | 8.7 | 8.0 | 7.9 |
| NM 375 | 7.0 | 7.3 | 7.3 | 8.0 | 9.0 | 8.3 | 7.8 |
| MSB-10 | 7.3 | 7.0 | 8.0 | 8.0 | 8.0 | 7.7 | 7.7 |
| NM 507 | 6.7 | 8.0 | 7.7 | 7.0 | 8.3 | 8.0 | 7.6 |
| MSB-30 | 7.3 | 8.0 | 7.0 | 6.3 | 9.0 | 8.0 | 7.6 |
| NM 471 | 6.3 | 7.7 | 7.7 | 7.7 | 8.0 | 8.0 | 7.6 |
| Tufcote | 6.7 | 6.7 | 6.7 | 6.7 | 7.7 | 8.3 | 7.1 |
| NMS 3 | 5.7 | 7.0 | 7.0 | 6.7 | 8.0 | 8.0 | 7.1 |
| Texturf 10 | 6.7 | 6.7 | 7.0 | 6.3 | 7.7 | 8.0 | 7.1 |
| Midiron | 4.0 | 6.7 | 7.7 | 8.3 | 7.3 | 8.0 | 7.0 |
| NMS 4 | 6.3 | 6.3 | 6.7 | 6.7 | 8.3 | 7.7 | 7.0 |
| A-29 | 6.0 | 6.0 | 7.3 | 7.0 | 7.0 | 7.3 | 6.8 |
| Midlawn (A-22) | 5.7 | 5.3 | 6.7 | 7.0 | 7.7 | 8.0 | 6.7 |
| MSB-20 | 6.3 | 6.7 | 6.7 | 6.7 | 7.0 | 6.7 | 6.7 |
| Tifgreen | 6.3 | 6.3 | 6.7 | 6.3 | 7.0 | 7.3 | 6.7 |
| NM 72 | 5.3 | 7.0 | 6.7 | 6.0 | 7.3 | 7.3 | 6.6 |
| Midfield (E-29) | 5.3 | 5.7 | 7.0 | 6.7 | 6.3 | 8.0 | 6.5 |
| FB-119 | 5.3 | 6.3 | 6.7 | 6.3 | 7.3 | 7.0 | 6.5 |
| Guymon | 4.7 | 6.0 | 6.7 | 7.0 | 7.3 | 7.3 | 6.5 |
| CT-23 | 5.3 | 6.0 | 6.7 | 6.7 | 7.0 | 7.0 | 6.4 |
| NM 43 | 5.7 | 6.3 | 6.0 | 5.7 | 8.0 | 6.3 | 6.3 |
| Numex-Sahara | 5.3 | 5.3 | 5.7 | 5.7 | 8.0 | 7.7 | 6.3 |
| NMS 2 | 5.3 | 5.3 | 6.0 | 5.7 | 7.0 | 7.3 | 6.1 |
| Vamont | 5.0 | 5.3 | 6.7 | 6.0 | 7.3 | 6.3 | 6.1 |
| RS-1 | 4.3 | 5.7 | 7.0 | 6.0 | 7.0 | 6.3 | 6.1 |
| NMJS 14 | 4.7 | 4.7 | 6.3 | 5.0 | 7.0 | 7.3 | 5.8 |
| AZ Common | 5.0 | 4.0 | 5.7 | 5.7 | 7.3 | 7.0 | 5.8 |
| LSD VALUE | 1.6 | 1.0 | 0.7 | 0.9 | 0.7 | 0.8 | 0.4 |

[1]To determine statistical differences among entries, subtract one entry's mean from another. Statistical differences occur when this value is larger than the corresponding LSD value (LSD 0.05).

TABLE 7

Leaf Texture Ratings of Bermudagrass Cultivars, 1990[1]

| Bermuda clone | Leaf Texture Ratings (1–9, 9 = very fine) AR1 | AZ1 | LA1 | Mean |
|---|---|---|---|---|
| MSB-20 | 8.7 | 8.0 | 9.0 | 8.6 |
| Tifway II | 8.3 | 8.0 | 9.0 | 8.4 |
| MSB-10 | 8.3 | 8.0 | 8.7 | 8.3 |
| NM 43 | 7.7 | 8.0 | 8.7 | 8.1 |

TABLE 7-continued

Leaf Texture Ratings of Bermudagrass Cultivars, 1990[1]

| Bermuda clone | Leaf Texture Ratings (1-9, 9 = very fine) AR1 | AZ1 | LA1 | Mean |
|---|---|---|---|---|
| Tifway | 7.7 | 8.0 | 8.7 | 8.1 |
| Tifgreen | 8.3 | 7.3 | 8.0 | 7.9 |
| Midlawn (A-22) | 7.3 | 8.0 | 8.0 | 7.8 |
| CT-23 | 6.3 | 7.7 | 8.3 | 7.4 |
| NM 471 | 6.0 | 7.0 | 8.3 | 7.1 |
| NM 507 | 6.0 | 7.0 | 8.0 | 7.0 |
| Tufcote | 7.0 | 6.3 | 7.7 | 7.0 |
| NM 72 | 6.0 | 7.0 | 7.3 | 6.8 |
| NMS 3 | 6.3 | 7.0 | 7.0 | 6.8 |
| NMS 4 | 6.0 | 7.0 | 7.0 | 6.7 |
| A-29 | 6.0 | 6.7 | 7.0 | 6.6 |
| FB-119 | 5.7 | 7.0 | 7.0 | 6.6 |
| MSB-30 | 6.0 | 6.7 | 7.0 | 6.6 |
| NM 375 | 6.0 | 6.7 | 7.0 | 6.6 |
| Midiron | 6.3 | 6.3 | 7.0 | 6.6 |
| Texturf 10 | 5.3 | 6.3 | 7.7 | 6.4 |
| Midfield (E-29) | 6.3 | 6.3 | 6.0 | 6.2 |
| Numex-Sahara | 5.0 | 6.0 | 7.0 | 6.0 |
| AZ Common | 6.3 | 5.3 | 6.0 | 5.9 |
| NMS 2 | 4.7 | 5.7 | 6.3 | 5.6 |
| RS-1 | 4.7 | 6.0 | 6.0 | 5.6 |
| Vamont | 4.7 | 5.7 | 5.3 | 5.2 |
| NMS 14 | 4.3 | 5.3 | 5.7 | 5.1 |
| Guymon | 3.3 | 5.7 | 5.3 | 4.8 |
| LSD VALUE | 1.2 | 0.7 | 0.6 | 0.5 |

[1]To determine statistical differences among entries, subtract one entry's mean from another. Statistical differences occur when this value is larger than the corresponding LSD value (LSD 0.05).

TABLE 8

Summer Density Ratings of Bermudagrass Cultivars, 1990[1]

| Bermuda clone | Density Ratings (1-9, 9 = maximum density) AR | Mean |
|---|---|---|
| MSB-20 | 9.0 | 9.0 |
| Tifway | 9.0 | 9.0 |
| Tifway II | 9.0 | 9.0 |
| MSB-10 | 8.7 | 8.7 |
| Tufcote | 8.0 | 8.0 |
| Midlawn (A-22) | 7.7 | 7.7 |
| NM 375 | 7.7 | 7.7 |
| NM 43 | 7.7 | 7.7 |
| NM 471 | 7.7 | 7.7 |
| NM 507 | 7.7 | 7.7 |
| Texturf 10 | 7.7 | 7.7 |
| Tifgreen | 7.7 | 7.7 |

TABLE 8-continued

Summer Density Ratings of Bermudagrass Cultivars, 1990[1]

| Bermuda clone | Density Ratings (1-9, 9 = maximum density) AR | Mean |
|---|---|---|
| A-29 | 7.3 | 7.3 |
| FB-119 | 7.3 | 7.3 |
| MSB-30 | 7.0 | 7.0 |
| NM 72 | 7.0 | 7.0 |
| Midfield (E-29) | 6.7 | 6.7 |
| Midiron | 6.7 | 6.7 |
| NMS 3 | 6.7 | 6.7 |
| NMS 4 | 6.7 | 6.7 |
| RS-1 | 6.7 | 6.7 |
| CT-23 | 6.3 | 6.3 |
| AZ Common | 5.7 | 5.7 |
| NMS 2 | 5.7 | 5.7 |
| Vamont | 5.7 | 5.7 |
| Numex-Sahara | 5.0 | 5.0 |
| NMS 14 | 5.0 | 5.0 |
| Guymon | 4.3 | 4.3 |
| LSD VALUE | 1.1 | 1.1 |

[1]To determine statistical differences among entries, subtract one entry's mean from another. Statistical differences occur when this value is larger than the corresponding LSD value (LSD 0.05).

TABLE 9

Evaluation of Bermudagrass Clones at the Horticulture Research Center, Wichita, KS for Susceptibility to Spring Dead Spot

| Bermuda clone[1] | Number of Spots | % Area w/Spots | % Kill in Spots | Total Plot Quality[2] |
|---|---|---|---|---|
| Midiron | 2.0 | 4.0 | 26.7 | 8.7 |
| Midlawn (A-22) | 1.3 | 6.2 | 21.7 | 9.0 |
| Midfield (E-29) | 2.3 | 7.8 | 26.7 | 8.0 |
| A-29 | 2.3 | 12.9 | 33.3 | 8.0 |
| Guymon | 2.7 | 10.0 | 70.0 | 6.0 |
| Midway | 2.0 | 11:5 | 43.3 | 7.0 |
| RS-1 | 3.3 | 20.6 | 70.0 | 6.3 |
| Texturf 10 | 3.0 | 24.7 | 96.7 | 5.7 |
| Vamont | 3.3 | 26.1 | 95.0 | 4.6 |
| Sunturf | 3.3 | 32.7 | 90.0 | 4.7 |
| Tifgreen | 4.0 | 36.11 | 98.3 | 4.0 |
| LSD (P = 0.05) | 0.3 | 14.7 | 17.0 | 1.4 |

[1]Other clones in test with complete winter kill in at least two of the three replicated plot included CT-23, NM 43, NM72, NM375, NM 471, NM507, MSB-10, MSB-20, MSB-30, Tufcote, Tifway, Tifway II, NMS1, NMS3, NMS4, NMS14, Arizona Common, and FB119.

[2]Plot quality rating where 0 = complete kill of plot, and 9 = 90% or better coverage of plot.

Having thus described the invention, the following is claimed as new and desired to be secured by Letters Patent:

1. A new and distinct variety of Bermudagrass as shown and described.

* * * * *